(12) United States Patent
Butcher et al.

(10) Patent No.: US 10,119,951 B2
(45) Date of Patent: Nov. 6, 2018

(54) ON-LINE WET CHEMISTRY ANALYZER

(71) Applicant: Rosemount Inc., Shakopee, MN (US)

(72) Inventors: Bradley A. Butcher, La Verne, CA (US); Hoang Minh Nguyen, Highland, CA (US); Chang-Dong Feng, Long Beach, CA (US)

(73) Assignee: Rosemount Inc., Shakopee, MN (US)

( * ) Notice: Subject to any disclaimer, the term of this patent is extended or adjusted under 35 U.S.C. 154(b) by 0 days.

(21) Appl. No.: 14/852,008

(22) Filed: Sep. 11, 2015

(65) Prior Publication Data

US 2016/0077076 A1     Mar. 17, 2016

Related U.S. Application Data

(60) Provisional application No. 62/049,760, filed on Sep. 12, 2014.

(51) Int. Cl.
*G01N 21/01*          (2006.01)
*G01N 33/18*          (2006.01)
(Continued)

(52) U.S. Cl.
CPC ........... *G01N 33/18* (2013.01); *G01N 1/4077* (2013.01); *G01N 21/01* (2013.01); *G01N 31/02* (2013.01);
(Continued)

(58) Field of Classification Search
CPC .. G01N 21/3504; G01N 21/766; G01N 21/76; G01N 33/0037; G01N 21/05;
(Continued)

(56) References Cited

U.S. PATENT DOCUMENTS 3,193,355 A    7/1965   Fuhmann
3,773,423 A    11/1973   Hach
(Continued)

FOREIGN PATENT DOCUMENTS

JP         S6166951 A     4/1986
JP    2003-098092 A     4/2003
(Continued)

OTHER PUBLICATIONS

International Search Report and Written Opinion for International Application No. PCT/US2015/049732, dated Dec. 22, 2015, date of filing: Sep. 11, 2015, 14 pages.
(Continued)

*Primary Examiner* — Jennifer Wecker
(74) *Attorney, Agent, or Firm* — Christopher R. Christenson; Kelly, Holt & Christenson PLLC (57) ABSTRACT

A wet chemistry analyzer is provided. The wet chemistry analyzer comprises a reaction chamber configured to receive a reactant solution from a sample inlet and facilitate a process reaction. The wet chemistry analyzer also includes a detection chamber configured to receive a portion of a reaction mixture from the reaction chamber and measure a concentration of a chemical within the reaction mixture. The reaction chamber and the detection chamber are fluidically coupleable such that a portion of the reaction mixture can be directed to flow into the detection chamber to pre-condition a surface inside the detection chamber.

7 Claims, 7 Drawing Sheets

(51) Int. Cl.
  *G01N 1/34* (2006.01)
  *G01N 31/02* (2006.01)
  *G01N 1/40* (2006.01)
  *G01J 4/04* (2006.01)
  *G01N 21/31* (2006.01)
  *G01N 21/21* (2006.01)

(52) U.S. Cl.
  CPC ............... *G01J 4/04* (2013.01); *G01N 21/21* (2013.01); *G01N 21/3103* (2013.01); *G01N 2201/062* (2013.01); *G01N 2201/0612* (2013.01); *G01N 2201/127* (2013.01)

(58) Field of Classification Search
  CPC ............ G01N 21/3554; G01N 21/01; G01N 21/3103; G01N 21/643; G01N 21/75; G01N 21/85; G01N 31/005; G01N 33/52; G01N 1/34; G01N 1/4077; G01N 21/21; G01N 2201/0612; G01N 2201/062; G01N 2201/127; G01N 31/02; G01N 33/18; Y10T 137/87161; G01J 4/04
  See application file for complete search history.

(56) References Cited

U.S. PATENT DOCUMENTS

| | | | |
|---|---|---|---|
| 4,131,428 A | 12/1978 | Diggens | |
| 4,251,218 A | 2/1981 | Diggens | |
| 4,263,104 A | 4/1981 | Diggens et al. | |
| 4,293,316 A * | 10/1981 | Block | G01N 1/34 73/31.07 |
| 4,865,811 A * | 9/1989 | Newton | G01N 35/085 422/81 |
| 4,865,992 A | 9/1989 | Hach et al. | |
| 5,230,863 A | 7/1993 | Salpeter | |
| 5,300,442 A | 4/1994 | Frant | |
| 5,487,871 A * | 1/1996 | McDow | G01N 21/01 422/231 |
| 6,306,284 B1 | 10/2001 | Yang et al. | |
| 7,381,564 B2 | 6/2008 | Matschenko et al. | |
| 7,842,510 B2 | 11/2010 | Shimizu et al. | |
| 2005/0196319 A1 | 9/2005 | Bogren et al. | |
| 2006/0133964 A1 | 6/2006 | Bailey et al. | |
| 2011/0165595 A1* | 7/2011 | Catanzaro | B01L 7/52 435/7.21 |

FOREIGN PATENT DOCUMENTS

| | | |
|---|---|---|
| WO | WO2009144331 A1 | 12/2009 |
| WO | WO 2013-184584 A1 | 12/2013 |

OTHER PUBLICATIONS

First Office Action for Chinese Patent Application No. 201580002314.8, dated Oct. 31, 2016, 19 pages.
International Preliminary Report on Patentability for PCT US2015/049732 dated Mar. 23, 2017, 10 pages.
Second Office Action for Chinese Patent No. 201580002314.8, dated Jun. 15, 2017, 23 pages including English translaton.
First Examination Report for Australian Patent Application No. 2015314799, dated Oct. 27, 2017, 4 pages.
Office Action dated Mar. 16, 2018, for Canadian Patent Application No. 2,960,530, 4 pages.
Search Report dated Jun. 25, 2018, for European Patent Application No. 15840079.6, 15 pages.

* cited by examiner

ON-LINE WET CHEMISTRY ANALYZER

CROSS-REFERENCE TO RELATED APPLICATION

The present application is based on and claims the benefit of U.S. Provisional Patent Application Ser. No. 62/049,760, filed Sep. 12, 2014, the content of which is hereby incorporated in its entirety.

BACKGROUND

On-line wet chemistry analyzers are used in a variety of industries to provide a continuous indication of a chemical in a process sample. This continuous indication can be provided locally by the analyzer and/or remotely to one or more suitable devices in order to provide control and/or monitoring of a chemical process.

One particular type of on-line wet chemistry analyzer is an on-line silica analyzer. These devices are configured to generate a reaction in the process sample that allows an indication of silica in the sample to be determined. Such analyzers are useful in determining silica content in boiler water, boiler feed water, demineralized water, and steam condensate. While such analyzers are useful in a variety of industries, they are of particular use in power plant boilers. In such systems, silica can form silicate deposits that can damage turbines and other generation equipment that are used in the water steam turbine cycle. Accordingly, power plants with high pressure turbines generally monitor silica carefully in order to ensure effective detection and removal/remediation. However, while the present discussion focuses on an exemplary silica analyzer, the methods and embodiments described herein may be applicable to analyzers drawn to measuring concentrations of other chemicals.

The discussion above is merely to provide for general background information, and is not intended to be used as an aid in determining the scope of the claimed subject matter.

SUMMARY

A wet chemistry analyzer is provided. The wet chemistry analyzer comprises a reaction chamber configured to receive a reactant solution from a sample inlet and facilitate a process reaction. The wet chemistry analyzer also includes a detection chamber configured to receive a portion of a reaction mixture from the reaction chamber and measure a concentration of a chemical within the reaction mixture. The reaction chamber and the detection chamber are fluidically coupleable such that a portion of the reaction mixture can be directed to flow into the detection chamber to pre-condition a surface inside the detection chamber. These and various other features and advantages that characterize the claimed embodiments will become apparent upon reading the following detailed description and upon reviewing the associated drawings.

DETAILED DESCRIPTION

Colorimetric detection can be used to measure concentration of reactants, products or trace compounds of a reaction. In one embodiment, a reaction starts with one or more reactants that are, during a reaction period, converted at least partially to one or more products. Additionally, the reactants may be converted to one or more unwanted byproducts. A reaction is 'complete' at the end of a reaction time. Some reactions progress to completion, given enough time, such that all of the reactant molecules are converted to product molecules. Other reactions may only progress until an equilibrium is reached, such that there will always be some reactant molecules in a final reaction product, and the equilibrium achieved may also be considered a completion point. Many reactions have a known reaction rate, such that it can be predicted, based on that rate, when the reaction will reach completion. However, many factors such as adequate mixing, temperature, pressure, concentration of initial reactant or the presence of sufficient catalyst may affect the reaction rate. Therefore, it may be helpful, in one embodiment, for an analyzer to be configured to detect a completed reaction. As used herein, reactant solution refers to substantially unreacted solution provided at the beginning of a reaction. Reaction mixture may refer to a mixture within a reaction chamber at any point during the reaction period. Product solution refers to the mixture after the reaction has reached completion.

An on-line silica analyzer will generally employ a known reaction to render the silica in the process readily detectable by a colorimetric detection method. One example of such a reaction is known as the molybdenum blue method. In the molybdenum blue method, molybdate (usually in the form of potassium molybdate) is used to react with silica in the process sample/solution in order to generate a compound suitable for colorimetric detection. In accordance with the molybdenum blue method, the silica content in water is measured based on the color of the silicomolybdic acid formed through the wet chemistry process. The colorimetric detection, in accordance with the molybdenum blue method, is governed by the Beer-Lambert Law, which states that there is a logarithmic dependence between the transmission (or transmissivity), T, of light through a substance and the product of the absorption coefficient of the substance, α, and the distance that the light travels through the material (i.e. path length), 1. The Beer-Lambert law is expressed as follows:

$$T = \frac{I}{I_o} = 10^{-\alpha l} = 10^{-\epsilon l c} \qquad \text{Equation 1}$$

The absorption coefficient can be written as a product of the molar absorptivity (extinction coefficient) of the absorber, $\epsilon$, and the molar concentration, c, of the absorbing species in the material where I and $I_o$ are the intensity of the incident light and the transmitted light, respectively.

During the detection of low concentration of silica ($SiO_2$) at parts per billion (ppb) levels with molybdenum blue method, the adsorption of silica-molybdate complex on the surface of the reaction or detection chamber will always generate a discrepancy to the measurement, in other words, the measured concentration will always be less than the actual concentration due to the adsorption (take-away) of the silica-molybdate complex. As the surface of the detection chamber absorbs the silica-molybdate complex, the concentration of the solution changes, resulting in an artificially-low detected concentration. However, because the adsorption rate may not be consistent or known, the difference between the actual silica concentration, and the measured concentration, may not be a consistent or calculable number. A detection system is desired that can measure a current, accurate level of silica in a process stream.

Embodiments of the present invention generally provide an arrangement of a reaction chamber and a detection chamber and several flow path configurations that facilitate a colorimetric based wet chemistry analysis of silica concentration in a process stream. Embodiments described herein allow a parallel processing of blank sample preparation, pre-conditioning and reacted solution measurement. Using embodiments of the present invention, mixing of sample and reagents is performed by injecting air bubbles into the liquid in the reaction chamber. Meanwhile, the pressure created by the air is used to move the liquid in and out of the chambers.

Pre-conditioning of at least some, and preferably all surfaces of the analyzer that are subject to exposure by the reaction mixture or product solution significantly mitigates adsorption issues. This extra process step typically would add significantly to the length of each analysis cycle, however, embodiments of the present invention solve this time impact by employing bubble mixing that coincidently moves fluids within the manifold. Two chambers, reaction chamber and detection chamber, are employed to cause this to occur.

Figure 1:
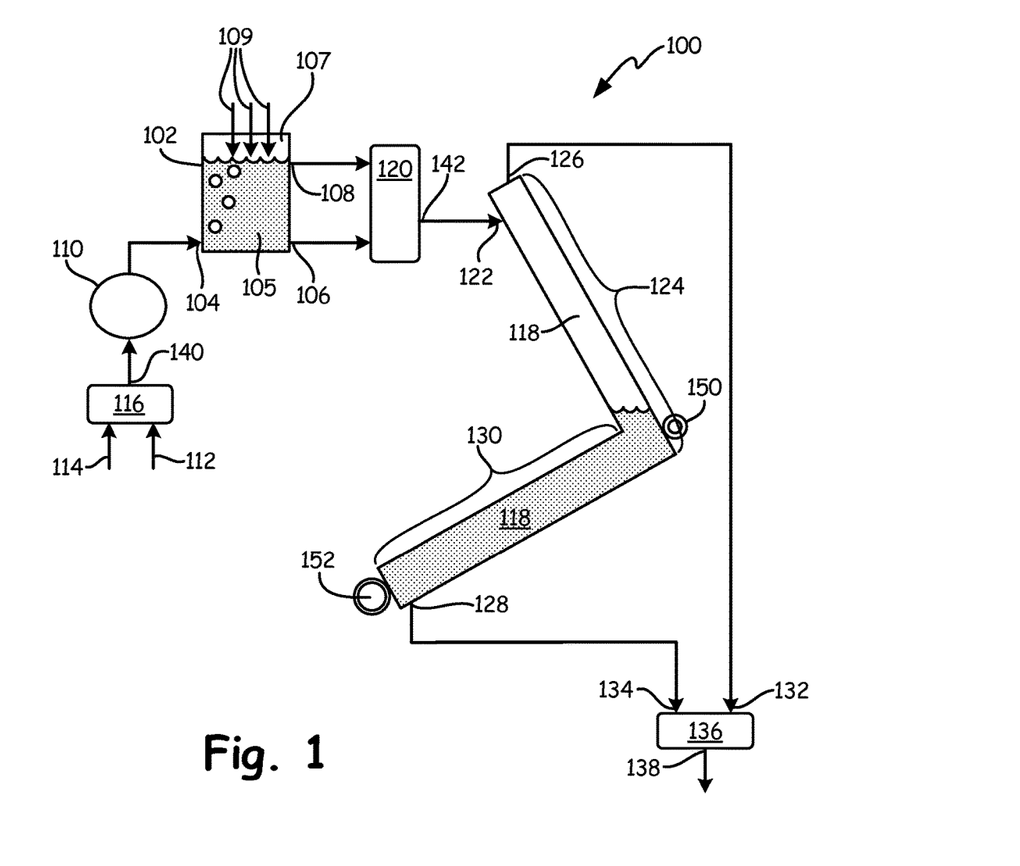
FIG. 1 is a diagrammatic view of a silica wet chemistry analyzer system that may be useful in one embodiment of the present invention.

FIG. 1 is a diagrammatic view of a silica wet chemistry analyzer system that may be useful in one embodiment of the present invention. Analyzer 100 comprises reaction chamber 102 that includes, in one embodiment, an inlet 104 connecting to a bottom portion 105 of the reaction chamber 102. Reaction chamber 102 may also have a first outlet 106 at a bottom portion 105 of reaction chamber 102, and a second outlet 108 at a top portion 107 of the reaction chamber 102. Inlet 104 may be connected to a pump 110, which may pump in either a reactant solution or air, or another suitable gas, through three way valve 116. In a first configuration, the three-way valve 116 connects a sample inlet 112 to the reaction chamber 102. In a second configuration, the three-way valve 116 connects the air inlet 114 to the reaction chamber 102 such that air, or another gas, can enter the reaction chamber 102, but that reactant solution cannot. In one embodiment, the analyzer 100 is configured such that air and the reactant solution cannot be simultaneously injected into the reaction chamber 102. In another embodiment, air may also be injected into the reaction chamber 102 from another source than the three-way valve 116.

The two outlets 106 and 108 of reaction chamber 102 are connected to a detection chamber 118 through a second three way valve 120. The common connection of three way valve 120, in one embodiment, is connected to inlet 122 of the detection chamber 118. In one embodiment, inlet 122 is located at a top portion 124 of the detection chamber 118. Detection chamber 118 may also have two outlets: outlet 126, and outlet 128. In one embodiment, outlet 126 is located in the top portion 124 of the detection chamber 118, and outlet 128 is located in a bottom portion 130 of the detection chamber 118. In one embodiment, the two outlets 126 and 128 are connected, respectively, to inlets 132 and 134 of a three way valve 136, with the common line of valve 136, line 138, being connected to a waste stream of the analyzer 100.

In one embodiment, changing the configuration of valve 116, valve 120 and/or valve 136, alters a flow path of fluids throughout the analyzer 100. In one embodiment, changing the configuration of these three valves allows for the reaction chamber 102 to facilitate a reaction process, while also facilitating pre-conditioning and sample detection in the detection chamber 118 such that, at the end of a reaction process in the reaction chamber 102, the detection chamber 118 has been pre-conditioned and is ready to receive the reaction mixture and determine an accurate concentration of silica within the reaction mixture or product solution.

One advantage of the system 100 presented in FIG. 1 is that the combination of two chambers allows for the pre-conditioning to occur in the detection chamber 118 in parallel to the reaction process within the reaction chamber 102. The reaction process conducted in parallel may comprise any, or all, of the steps of providing reactants and providing mixing agents to the reaction chamber 102, and allowing the reaction to proceed to completion.

Figure 2:
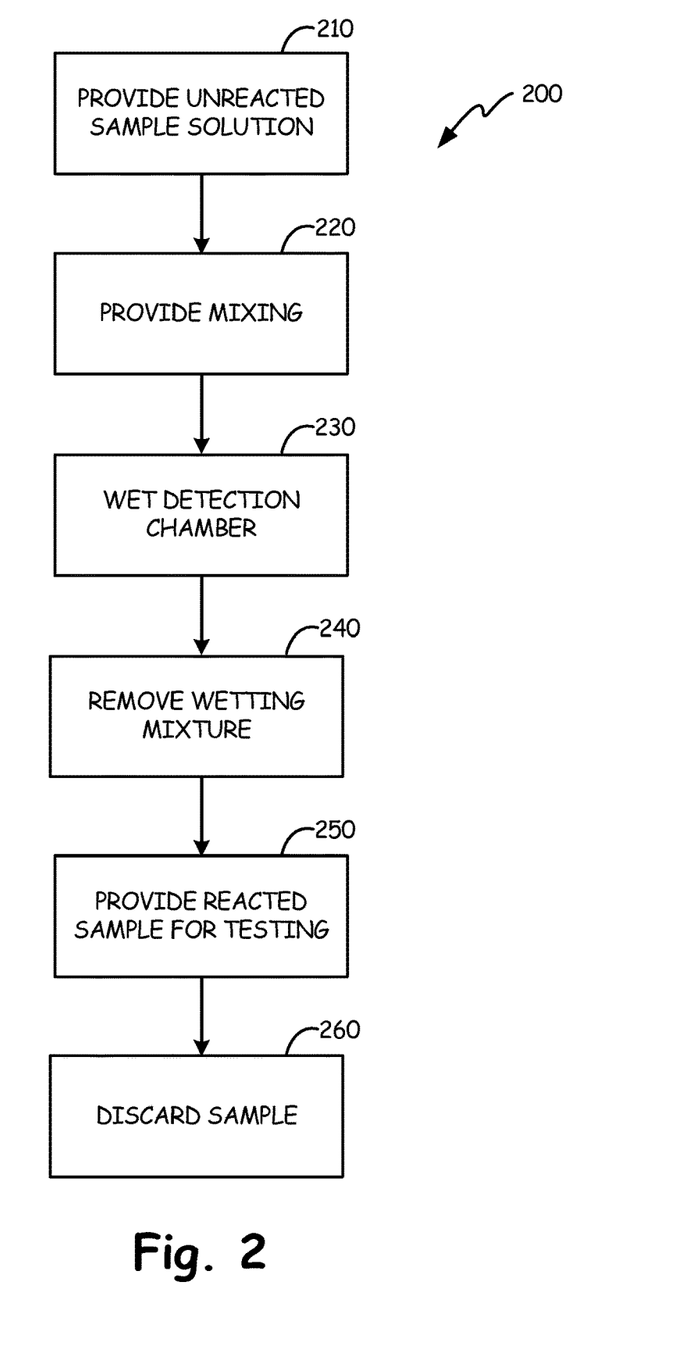
FIG. 2 illustrates a method of pre-conditioning a detection chamber of a silica wet chemistry analyzer system that may be useful in one embodiment of the present invention.

FIG. 2 illustrates an exemplary method for pre-conditioning a detection chamber during a reaction sequence. In one embodiment, the method 200 begins at block 210 with a reactant solution being provided to an analyzer, for example, analyzer 100. Other reactants may also be provided to the reaction chamber 102.

In block 220 a mixing agent is provided to the reaction mixture within the reaction chamber, for example reaction chamber 102. In one embodiment, the mixing agent is air, or another gas, provided from inlet 114. In another embodiment, the mixing agent is provided from another source. The mixing agent may also comprise, in one embodiment, another reactant.

In block 230, the detection chamber 118 is provided with a portion of the reaction mixture from the reaction chamber 102. In one embodiment, the reaction mixture is only partially reacted, and is provided to the detection chamber 118 while the reaction process is ongoing. In one embodiment, the reaction mixture provided is substantially equivalent to the reactant solution provided to the reaction chamber 102 through inlet 112 and is provided shortly after the start of a reaction in the reaction chamber 102. In another embodiment, the reaction mixture is provided to the detection chamber 118 after the reaction has started, but before the reaction process is complete. In a further embodiment, the reaction mixture is provided to the detection chamber 118 shortly before the conclusion of the reaction process, such that the reaction mixture provided is substantially the same as the product solution. The delivery of the reaction mixture to the detection chamber 118 could be automated, in one embodiment, to occur after a set time period from the beginning of the reaction process, or the delivery of the reactant solution to the reaction chamber 102. In another embodiment, delivery of the reaction mixture is accomplished manually by an operator of the analyzer 100.

In block 240, the pre-conditioning mixture is removed from the detection chamber 118. The removal may be configured to occur shortly before a projected end of a reaction process in the reaction chamber 102. The removal may occur automatically, or may be configured to be accomplished manually by an operator of the analyzer 100. In one embodiment, the pre-conditioning mixture comprises the reaction mixture provided to the detection chamber 118 less any adsorbed silica.

In block 250, a portion of the product solution is provided to the detection chamber 118. In one embodiment, the whole of the product solution moves through the detection chamber 118 prior to collection, for example, for further processing. In another embodiment, only a portion of the product solution moves through the detection chamber 118, while the remainder is removed from the reaction chamber 102 through another outlet. In one embodiment, the majority of the product solution is retained within the reaction chamber 102 until a concentration of silica is detected in the detection chamber 118 and compared to a pre-set concentration indicating a completion of the reaction has been reached. If the concentration detected indicates that the reaction is not complete, method 200 allows the reaction to continue in the reaction chamber 102 uninterrupted. The ability to measure concentration of silica in the reaction chamber 102 periodically while the reaction is ongoing eliminates the need to stop and restart the reaction process to facilitate sampling of the reaction mixture until the product solution, indicating completion, is detected.

In one embodiment, as shown in FIG. 1, detection of a silica concentration within the reaction mixture or product solution is accomplished within the detection chamber 118. The detection chamber 118 is configured such that, within the chamber 118 the reacted sample is exposed on one end to a light source 150 which propagates light throughout the detection chamber 118 such that it is detected by light detector 152. In this way, transmissivity of the light through the detection chamber 118 can be measured, and a concentration of silica within the reacted sample can be calculated. In one embodiment, this measurement is employed with the Beer-Lambert Law expressed in Equation 1 above, to provide a silica concentration output. In one embodiment, the reaction mixture that is processed through the detection chamber 118 is then pushed out of the detection chamber 118 into a waste line 138 of the analyzer 100. However, in another embodiment, the rest of the reaction mixture within the reaction chamber 102 is removed through a different outlet directly from the reaction chamber 102, and does not pass through the detection chamber 118.

FIGS. 3A-E illustrate diagrammatic configurations of a silica wet chemistry analyzer during different stages of a pre-conditioning process that may be useful in one embodiment of the present invention. In one embodiment, the configurations in FIGS. 3A-E correspond to different steps of the method 200 described above. The configurations in FIGS. 3A-E may be obtained by altering the configurations of the three-way valves 116, 120 and 136.

Figure 3A:
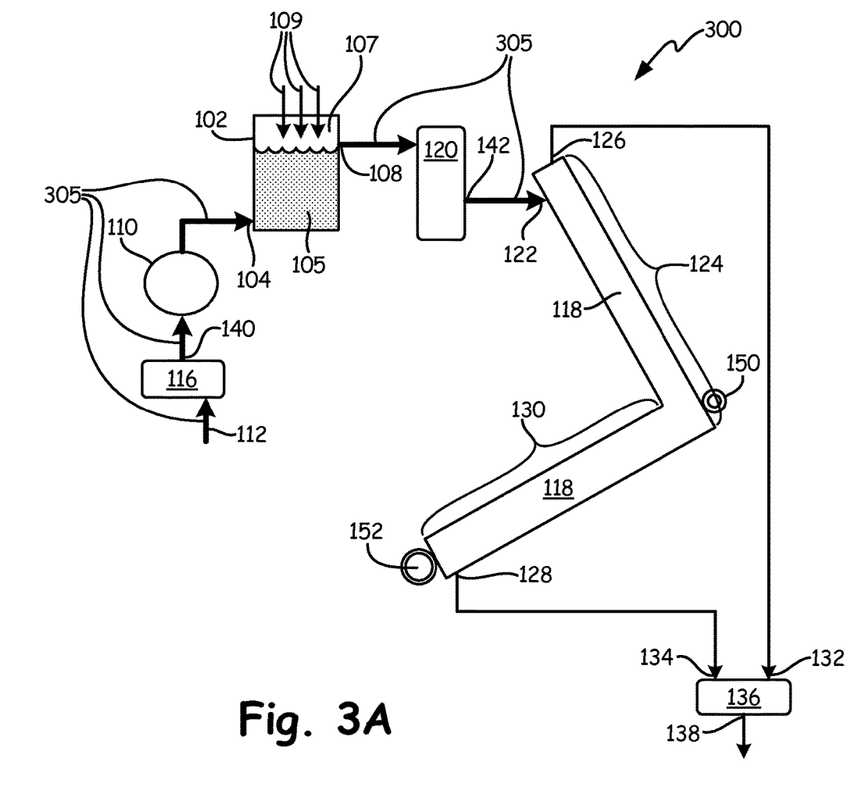
FIGS. 3A-E are diagrammatic views of embodiments of the present invention during different stages of an exemplary pre-conditioning process that may be useful in one embodiment of the present invention.

FIG. 3A illustrates a configuration 300 that is configured to direct flow through the analyzer 100 at least along a path 305 through the analyzer 100. In one embodiment, the common line 140 of valve 116 is connected such that sample input 112 is connected to the reaction chamber 102, allowing for reactant solution to flow into the reaction chamber 102. In one embodiment, configuration 300 allows for the reaction chamber 102 to fill with reactant solution. In one embodiment, valve 120 is configured such that outlet 108 is connected to allow excess air or gas to flow from the reaction chamber 102 through to the detection chamber 118, or otherwise out of the reaction chamber 102 through another outlet. However, in another embodiment, valve 120 may be configured such that neither outlet 108 or 106 is open from the reaction chamber 102, allowing the reaction chamber 102 to fill with reactant solution and any other reagents necessary to facilitate the desired reaction. In configuration 300, sample solution is able to flow from a reagent storage tank, or other unreacted sample solution tank, into the reaction chamber 102.

Figure 3B:
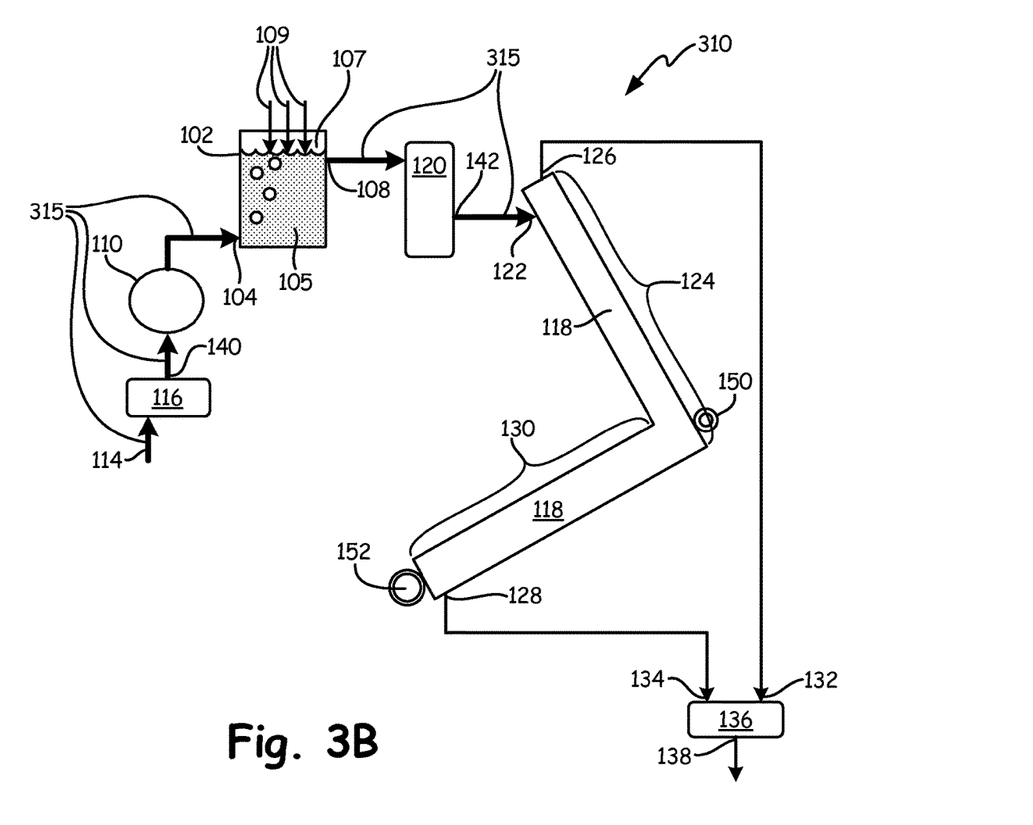

FIG. 3B illustrates a configuration 310 that directs flow through the analyzer 100 at least along a path 315. In one embodiment, configuration 310 allows for air, or other gas to enter the reaction chamber 102 from air inlet 114. This is accomplished by a configuration of valve 116 such that common line 140 is connected to the air inlet line 114. In one embodiment, valve 120 is configured such that common line 142 is connected with outlet 108, allowing for extra air or other gas flow to exit the reaction chamber 102 and flow into the detection chamber 118. In one embodiment, air is provided through air inlet 114 to reaction chamber 102 through inlet 104, located at a bottom portion 105 of the reaction chamber 102. In this way, air bubbles up into the reaction chamber 102, providing, in one embodiment, a mixing function. In one embodiment, this mixing function provides an additional advantage as solid or liquid reagents are added through reagent ports 109 into the reaction chamber 102. However, in another embodiment, gaseous reagents may be provided along with, or instead of the air into the system through inlet 114. In such an embodiment, this may allow for additional mixing and rapid reaction as the reagents are provided such that they bubble up through the sample solution in the reaction chamber 102.

Figure 3C:
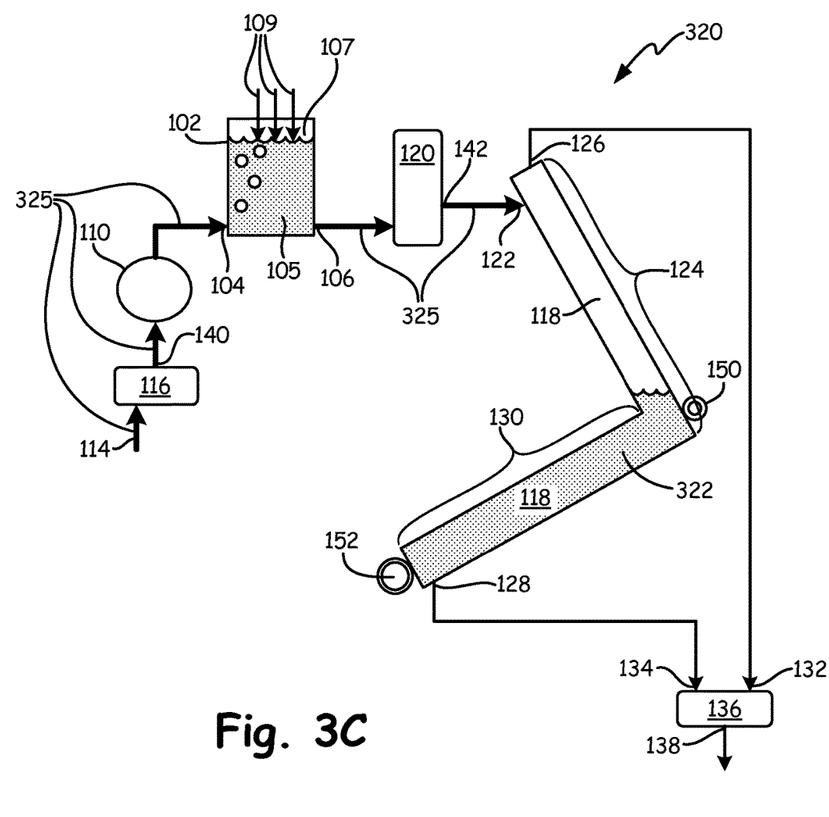

FIG. 3C illustrates a configuration 320 that directs flow through the analyzer 100 at least along a path 325. In one embodiment, valve 116 is configured such that common line 140 is connected to an air inlet 114. Valve 120 may be configured, in one embodiment, such that outlet 108 is connected to common line 142. Configuration 320 may allow, in one embodiment, for some reaction mixture to leave the reaction chamber 102 and flow into the detection chamber 118. This may be facilitated, in one embodiment, by gravity. In another embodiment, however, the reactant solution may be pushed through the reaction chamber 102 by the pressure of air flow from air inlet 114. In one embodiment, configuration 320 may further include valve 136 configured such that common line 138 is connected to outlet 132, providing that the detection chamber 118 fills with reaction mixture 322.

Figure 3D:
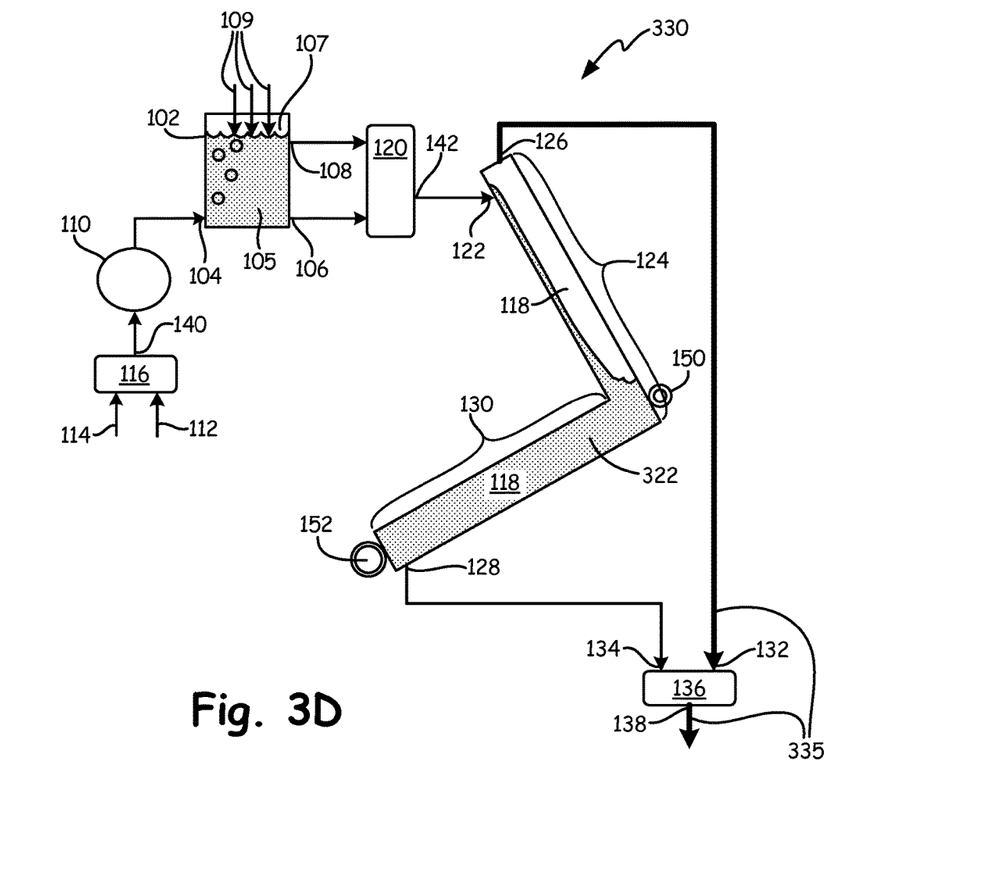

FIG. 3D illustrates an exemplary configuration 330 that directs flow through the analyzer 100 at least along a path 335. In one embodiment, for example, while reaction is occurring in reaction chamber 102, a pre-conditioning phase is occurring with the detection chamber 118. In one embodiment, common line 138 of valve 136 may be connected to outlet 126. This may allow for configurations 300 and 310 to be alternated between, for example, by a user of the analyzer 100, allowing for the reaction chamber 102 to be filled with sample solution and/or air, without disturbing the solution that has already been transferred to the detection chamber 118. In one embodiment, the reaction mixture in the detection chamber 118 may need to sit for a period of time to allow for pre-conditioning to completely occur within the detection chamber 118.

Figure 3E:
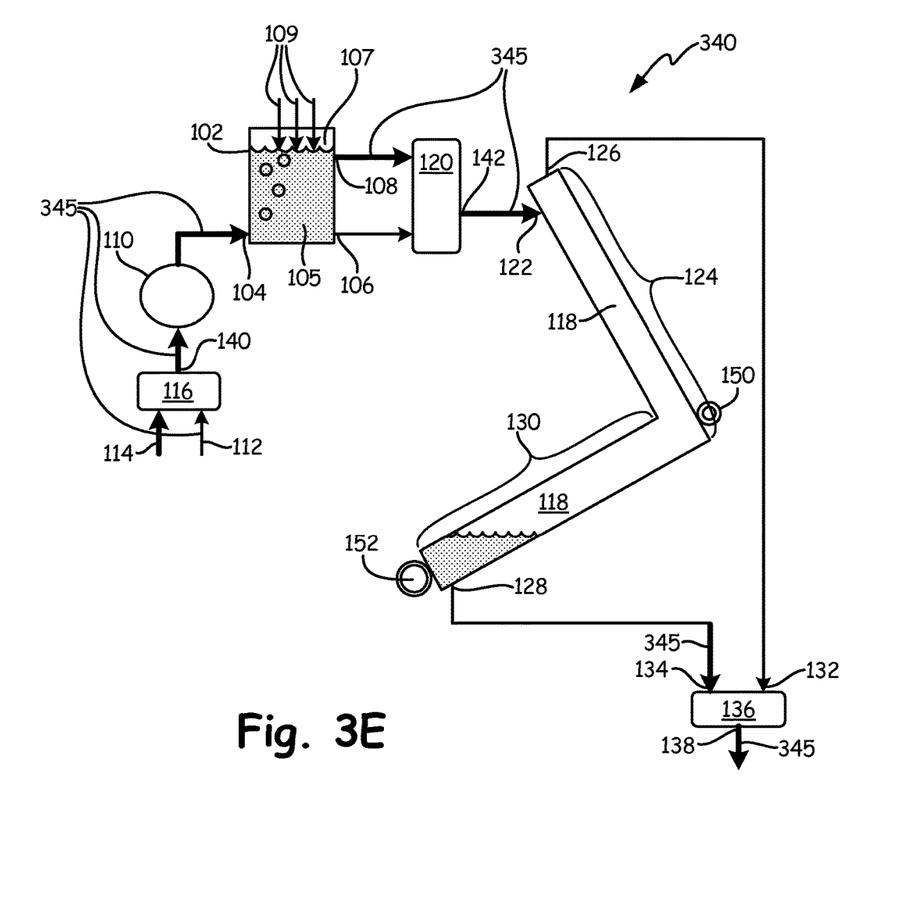

FIG. 3E illustrates a configuration 340 that directs flow through the analyzer 100 at least along a path 345. In configuration 340, common line 138 of valve 136 may be connected to outlet 128. In one embodiment of configuration 340, common line 142 of valve 120 is connected to outlet 108 of reaction chamber 102. In one embodiment of configuration 340, common line 140 of valve 116 is connected to the air inlet 114. In such a configuration as that of configuration 340, the reaction mixture in detection chamber 118 is drained into a waste, thus allowing a new batch of reaction mixture, or product solution, to be transferred to the detection chamber 118. This may be done, for example using configuration 320.

An advantage of a system of an analyzer containing both a detection chamber 118 and a reaction chamber 102, connected by a plurality of three-way valves such as valves 116, 120 and 136, is that it facilitates pre-conditioning. In one embodiment, a pre-conditioning process can occur within the detection chamber 118, for example as many times as necessary in order to ensure a correct reading of silica concentration within a reacted sample. The pre-conditioning processes can occur in tandem with a reaction in the reaction chamber 102, allowing for a more accurate silica reading without adding to an overall process time. In one embodiment, periodic samples may be taken of a reaction solution provided from reaction chamber 102 as the reaction continues during a reaction period. This may allow for continuous monitoring of the progress of a reaction in reaction chamber 102 without disturbing the reaction system. This may be advantageous, for example, in a batch reaction system, where otherwise disturbing and sampling the reaction chamber 102 could interfere with, or delay completion of the reaction.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A wet chemistry analyzer comprising:
   a reaction chamber configured to receive a reactant solution from a sample inlet and facilitate a process reaction;
   a detection chamber, fluidically connected, through a first three-way valve to the reaction chamber, wherein the detection chamber is configured to receives a portion of a reaction mixture from the reaction chamber while the process reaction is ongoing and before the process reaction is completed; and
   wherein the reaction chamber and the detection chamber are fluidically connected, through the first three-way valve, wherein the portion of the partially reacted reaction mixture is provided to the detection chamber and is configured to pre-condition a surface inside the detection chamber while the process reaction is occurring in parallel and proceeds to completion.

2. The analyzer of claim 1, and further comprising:
   a gas inlet fluidically connected to the reaction chamber, through a second three-way valve, wherein a gas flows into the reaction chamber from the gas inlet.

3. The analyzer of claim 2, wherein the gas flows into the reaction chamber at a position that it facilitates mixing within the reaction chamber.

4. The analyzer of claim 2, wherein the gas flows through the reaction chamber and the detection chamber and facilitates a partial removal of the portion of the reaction mixture from the detection chamber, through a third three-way valve, after the detection chamber surface is pre-conditioned.

5. The analyzer of claim 1, wherein the first three-way valve is alternatively causes a coupling between the detection chamber and either a liquid holding portion of the reaction chamber or a gas holding portion of the reaction chamber.

6. The analyzer of claim 1, wherein the detection chamber is also fluidically connected to a waste stream, through a third three-way valve that facilitates removal of the portion of the reaction mixture from the detection chamber prior to a second portion of the reaction mixture entering the detection chamber.

7. The analyzer of claim 1, wherein the reaction chamber is coupled to the detection chamber, and wherein the portion of the reaction mixture enters the detection chamber without significant disturbance to the ongoing process reaction.

* * * * *

UNITED STATES PATENT AND TRADEMARK OFFICE
CERTIFICATE OF CORRECTION

PATENT NO. : 10,119,951 B2
APPLICATION NO. : 14/852008
DATED : November 6, 2018
INVENTOR(S) : Bradley A. Butcher, Hoang Minh Nguyen and Chang-Dong Feng

Page 1 of 1

It is certified that error appears in the above-identified patent and that said Letters Patent is hereby corrected as shown below:

In the Claims

Column 8 Claim 5, Line 25: delete "is"

Signed and Sealed this
Tenth Day of March, 2020

Andrei Iancu
*Director of the United States Patent and Trademark Office*